US011364017B2

(12) United States Patent
Vincenot et al.

(10) Patent No.: US 11,364,017 B2
(45) Date of Patent: Jun. 21, 2022

(54) METHOD FOR COOLING AN ULTRASONIC PROBE AND PROBE INCLUDING SUCH COOLING

(71) Applicant: EDAP TMS FRANCE, Vaulx-en-Velin (FR)

(72) Inventors: Jérémy Vincenot, Villeurbanne (FR); Olivier Nallet, Lyons (FR); Emmanuel Blanc, Saint Didier au Mont d'Or (FR)

(73) Assignee: EDAP TMS FRANCE, Vaulx-en-Velin (FR)

( * ) Notice: Subject to any disclaimer, the term of this patent is extended or adjusted under 35 U.S.C. 154(b) by 337 days.

(21) Appl. No.: 16/605,582

(22) PCT Filed: Apr. 23, 2018

(86) PCT No.: PCT/FR2018/051013
§ 371 (c)(1),
(2) Date: Oct. 16, 2019

(87) PCT Pub. No.: WO2018/197795
PCT Pub. Date: Nov. 1, 2018

(65) Prior Publication Data
US 2020/0121299 A1    Apr. 23, 2020

(30) Foreign Application Priority Data

Apr. 24, 2017  (FR) ..................................... 17 53515

(51) Int. Cl.
*A61B 8/00* (2006.01)
*F28F 13/06* (2006.01)
(Continued)

(52) U.S. Cl.
CPC ............ *A61B 8/546* (2013.01); *A61B 8/4444* (2013.01); *A61B 8/4494* (2013.01); *F28F 13/06* (2013.01); *G10K 11/004* (2013.01); *A61N 7/02* (2013.01)

(58) Field of Classification Search
CPC ...... A61B 17/2251; A61B 2018/00023; A61B 8/4444; A61B 8/4494; A61B 8/546; A61N 7/02; F28F 13/06; G10K 11/004
See application file for complete search history.

(56) References Cited

U.S. PATENT DOCUMENTS 5,560,362 A    10/1996  Sliwa, Jr. et al.
6,126,619 A    10/2000  Peterson et al.
2011/0011111 A1  1/2011  Martin et al.

FOREIGN PATENT DOCUMENTS

EP    0 553 804 A2    8/1993
FR    2 910 169 A1    6/2008
(Continued)

OTHER PUBLICATIONS

International Search Report for PCT/FR2018/051013.
(Continued)

*Primary Examiner* — Mark D Remaly
(74) *Attorney, Agent, or Firm* — Ladas & Parry LLP; Malcolm J. MacDonald (57) ABSTRACT

A method for cooling a transducer of a probe for generating ultrasonic waves, the transducer exhibiting, at the front, a face (4) for emitting ultrasonic waves, and at the rear, a rear face (5), at least the emitting face partially delimiting a cooling chamber (11) wherein a cooling fluid circulates between at least an inlet (15) and at least an outlet (16), the inlet (15) being located at the periphery of the emitting face (4) whereas the outlet (16) is located in the central part of said emitting face. The method includes creating between the inlet (15) and the outlet (16), a circulation of cooling (Continued)

fluid according to a swirling inside the cooling chamber around the axis of acoustic propagation (A).

15 Claims, 7 Drawing Sheets

(51) Int. Cl.
*G10K 11/00* (2006.01)
*A61N 7/02* (2006.01)

(56) References Cited

FOREIGN PATENT DOCUMENTS

| | | |
|---|---|---|
| FR | 2 929 040 A1 | 9/2009 |
| JP | 2004-097402 A | 4/2004 |
| JP | 2007-144225 A | 6/2007 |

OTHER PUBLICATIONS

Written Opinion for PCT/FR2018/051013.
JP 2007 144225 A _ Espacenet English Translation.
JP 2004 097402 A _ Espacenet English Translation.
FR 2 910 169 A1_ Espacenet English Translation.
FR 2 929 040 A1_ Espacenet English Translation.

METHOD FOR COOLING AN ULTRASONIC PROBE AND PROBE INCLUDING SUCH COOLING

The present invention relates to the technical field of apparatuses or devices including an ultrasonic probe used for therapeutic treatment and able to possibly be associated with an ultrasonic probe for echographic imaging of the human anatomy.

The present invention aims more particularly the technique to cool a therapeutic ultrasonic probe or even an echographic one.

The object of the invention finds a particularly advantageous application in the field of therapeutic treatments by high-intensity focused ultrasonic waves (HIFU).

Generally, an ultrasonic probe includes an acoustic transducer composed of a material particularly piezoelectric which converts electric energy into mechanical energy. Due to the imperfect conversion efficiency, the non converted energy creates an accumulation of heat in the material of the transducer. A too high heat can lead to damage or even destruction of the transducer.

The state of the art proposes various techniques for dissipating the heat generated to lower the temperature of the transducer.

For example, patent EP 0553804 describes an ultrasonic medical transducer including a transducer element in contact with a heat conductive material to ensure cooling by thermal conduction towards the rear of the transducer. This passive-type cooling method, that is to say, without air or liquid circulation is relatively limited and adapted properly to transducers generating a few calories.

It is also known to use a cooling system of forced conduction type using a cooling fluid put into movement by a pump. For example, patent FR 2910169 describes an echography system including an echographic ultrasound and an active cooling system for evacuating heat from the probe. This cooling system includes a pump arranged to make a cooling agent circulate in the echographic probe. In the same manner, U.S. Pat. No. 5,560,362 describes an ultrasonic transducer provided with a cooling circuit including a heat exchanger and a pump ensuring closed loop circulation, of a cooling fluid for the transducer. In both cases, the cooling of the transducer is obtained by thermal conduction towards the rear of the transducer. The main drawback of this approach relates to the difficulty of incorporating, in the same rear volume, the cooling device and the control electronics of the transducer.

It is also known to use a cooling system of forced convection type using a cooling fluid put in movement by a pump. A main difficulty of a forced convection cooling system consists in obtaining homogenous cooling over the totality of the surface of the transducer. This difficulty is all the more emphasized when the transducer is far from a flat surface.

In the field of therapeutic ultrasonic probes generating important acoustic powers and energies, patent FR2929040 describes a transducer constituted of an assembly of several emitting elements, physically independent from each other. These electro-acoustic elements are placed between two discs forming a rear cooling chamber. One of the disks forms the front face of the transducer which contains the acoustic coupling fluid enclosed within a front chamber closed by a membrane. The other disk forms the rear face which receives the control electronics.

The transducer elements are each formed of a piezoelectric element fastened onto a solid electrically insulating and thermally conductive structure. This solid structure thus allows for draining thermal energy towards the rear of the transducer which thereby forms a sort of radiator when it is exposed to a cooling fluid.

The transducer elements are distributed according to spirals centered on the central part of the disk wherein the fluid outlet is provided, whereas the fluid inlets are provided at the periphery of the disk. Such a disposition allows obtaining, at a rear face of the transducer, a homogenous spiral flow due to the spiral disposition of the transducer elements. This cooling principle is specifically adapted for independent transducer elements able to form a conduction channel for the spiral cooling fluid. Such a cooling system proves to not be suitable for cooling via the front face of a transducer exhibiting a smooth emitting face whereon it is not possible to place element which could guide the liquid with a view to obtaining a homogenous flow as these elements would interfere with the ultrasonic field. In a complementary manner, the guided spiral circulation of cooling fluid does not allow to obtain an optimised cooling.

Document JP 2007144225 describes a therapeutic extra-corporeal ultrasonic system including a transducer in the shape of a narrow strip provided for intercostal treatment. This system also includes a cooling device by a liquid circulating by means of a suction pump and a discharge pump for maintaining a constant envelope volume of coupling liquid. FIGS. 14 to 23 describe different alternative embodiments of the cooling device.

FIGS. 14, 16 and 17 describe cooling liquid inlets at the periphery of the transducer with a cooling liquid jet deflection in the direction of the transducer with a discharge by a central orifice. Such a disposition ensures a centripetal circulation of cooling liquid that does not allow for opti-mised cooling.

In the embodiment example illustrated on FIG. 19, the injection nozzle is positioned to direct the cooling liquid in the direction of the ultrasonic transducer according to an oblique direction. The coupling liquid thus flows by turning inside the ultrasonic generator and by rising up to the central suction point. Such a turning centripetal circulation does not allow ensuring optimised cooling of the transducer. Furthermore, it is worth noting that the central non peripheral position of the injection nozzle interferes with the ultrasonic field of the transducer, thereby, harming its therapeutic performance.

The present invention aims to overcome the drawbacks of the prior art by proposing a new cooling technique for an ultrasonic probe allowing to obtain a homogenous optimised cooling of the transducer whatever the geometrical form of the transducer.

In order to attain such an objective, the invention relates to a method for cooling a transducer of a probe for generating ultrasonic waves, the transducer exhibiting, at the front, a face for emitting ultrasonic waves which propagate according to an axis of acoustic propagation, and at the rear, a rear face, at least the emitting face partially delimiting a cooling chamber wherein a cooling fluid circulates between at least an inlet and at least an outlet, the inlet being located at the periphery of the emitting face whereas the outlet is located in the central part of said emitting face According to the invention, the method consists in creating between the inlet and the outlet, a circulation of the cooling fluid according to a swirling inside the cooling chamber around the acoustic propagation axis of the emitting face of the transducer.

Another object of the invention is to propose a probe that generates ultrasonic waves, including a transducer, exhibiting, at the front, a face for emitting ultrasonic waves propagating along an acoustic propagation axis, and at the rear, a rear face, at least the emitting face partially delimiting a cooling chamber wherein a cooling liquid is brought, through a tubular duct, to circulate at least between an inlet located at the periphery of the emitting face and at least an outlet located in the central part of said emitting face, the tubular duct extending upstream from the inlet, with a length determined according a longitudinal extension axis to channel the cooling fluid with a velocity vector.

According to the invention, the tubular duct is oriented in such a manner that its longitudinal extension axis exhibits a non-null tangential component established according to a tangential direction substantially orthogonal to a plane containing the acoustic propagation axis and the inlet, to guide the fluid with a view to creating a circulation of cooling fluid according to a swirling inside the cooling chamber.

Moreover, the ultrasonic probe according to the invention can further include in combination with at least one and/or the other of the following additional features:
- the tubular duct is oriented so that its longitudinal extension axis and the velocity vector that it bears exhibits a tangential component such that the ratio of the tangential component of the velocity vector on the centripetal component of the velocity vector is greater than 1;
- the ultrasonic probe includes at the inlet, at least one deflecting wall for the fluid arranged facing the outlet of the tubular duct for orienting the fluid according to a tangential direction;
- the emitting face includes a peripheral edge located in a plane opening into an outlet, the tubular guiding duct for the cooling fluid, a fluid deflecting wall being arranged facing the outlet of the tubular duct;
- the peripheral edge of the emitting face is bordered at its periphery by a peripheral channel communicating with at least a tubular duct for supplying cooling fluid, this channel being provided with at least one centripetal opening for communicating with the cooling chamber;
- the ultrasonic probe includes several centripetal communication openings each delimited between two neighbouring wings for diverting the cooling fluid, with a curving profile varying from one tangent direction to a quasi-radial direction;
- the ultrasonic probe includes a tubular duct for supplying cooling fluid opening in the cooling chamber and exhibiting a straight passage section whereof the normal is confounded with the tangential direction;
- the cooling chamber includes a set of inlets distributed at the periphery of the emitting face, each having at least a tubular duct for the fluid, oriented according to a direction for creating together a swirling circulation of the cooling fluid inside the cooling chamber;
- the emitting face exhibits focusing geometry;
- the emitting face is truncated symmetrically with respect to an axis of acoustic propagation;
- the transducer includes in its central part, a second outlet for the cooling fluid, the two outlets preferably being, arranged symmetrically on either side of the axis of acoustic propagation of the emitting face;
- the transducer includes in its central part, a cutout delimiting a housing for an imaging probe on either side of which are located the outlets for the cooling fluid;
- the ultrasonic probe includes a fluid supply duct opening by the inlet in the cooling chamber, this duct including a device for controlling fluid velocity;
- the ultrasonic probe includes a temperature sensor adapted for measuring the temperature of the rear face of the transducer, this temperature sensor being connected to the device for controlling the fluid velocity allowing to control the inlet velocity of the fluid in the cooling chamber according to temperature measurement;
- the tubular duct exhibits a length greater than or equal to either its diameter for a duct of circular section, or the smallest diameter for a duct of oblong section or the smallest width for a duct of rectangular section.

Various other features will become apparent from the description made below with reference to the accompanying drawings which show, by way of non limiting examples, embodiments of the object of the invention.

The object of the invention relates to a new technique for cooling a probe 1 for generating ultrasonic waves. As it appears more precisely from FIGS. 1 and 2, this probe 1 is used more particularly for therapeutic treatment. This therapeutic probe 1 is part of a therapeutic apparatus in the general sense, not represented but known per se and adapted to carry out the treatment of tissues of a living being by means of ultrasonic waves. Advantageously, this therapeutic probe generates high-intensity focused ultrasound (HIFU). Obviously, the cooling technique in accordance with the invention can be implemented for a probe for generating ultrasonic therapeutic waves associated or not with an echographic imaging probe of the human anatomy.

Figure 1:
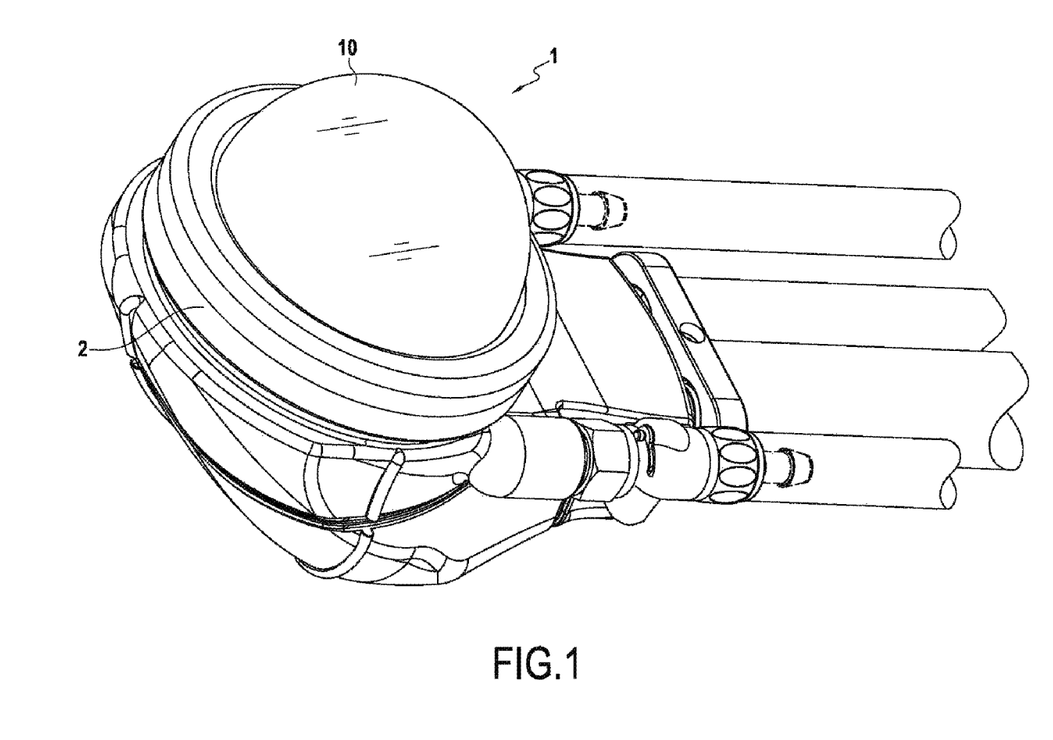
FIG. 1 is a perspective view showing an embodiment example of a therapeutic ultrasonic probe according to the invention.
Figure 2:
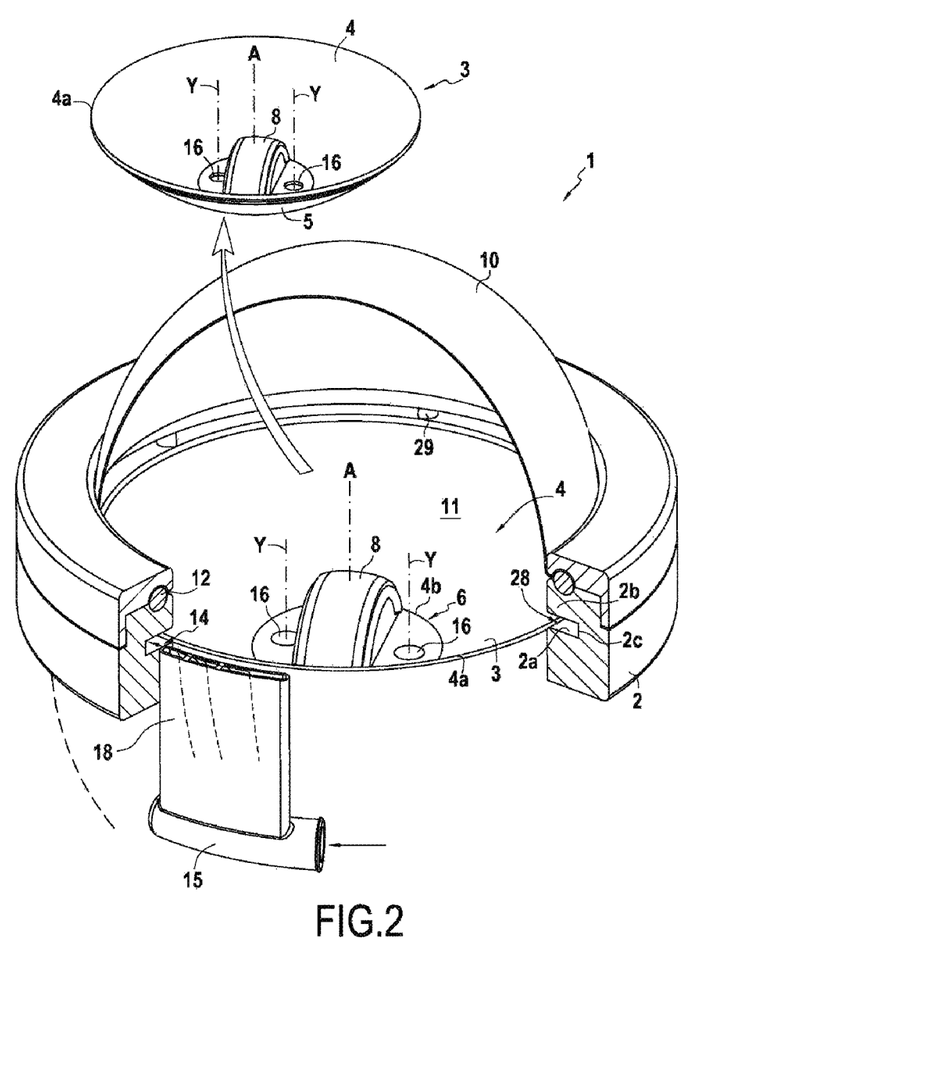
FIG. 2 is a partly cutaway view of the probe in FIG. 1.

The probe 1 particularly includes a supporting body 2 for a transducer 3 including one or several ultrasonic transmitters such as for example piezoelectric elements. The ultrasonic transmitters of the transducer 3 are connected via, an amplifying stage, to a control circuit delivering signals for activating the ultrasonic transmitters. The control circuit is not described in further detail as its performance is part of the technical knowledge of the skilled person. This control circuit thus typically includes a driven signal generator which is connected to the ultrasonic transmitters by means of the amplifying stage.

The transducer 3 exhibits, at the front, a face 4 for emitting ultrasonic waves, and at the rear, a rear face 5. According to an alternative embodiment, a temperature sensor can possibly be present on this rear face in order to measure the thermal heating at this surface. The emitting face 4 exhibits a smooth surface, by being delimited by a peripheral edge 4a and possibly by an inner edge 4b delimiting a cutout provided in the central part of the transducer.

Generally, the emitting face 4 has an axis of acoustic wave propagation A corresponding to the axis of symmetry and which will be designated in the rest of the description by an axis of acoustic propagation A. According to an advantageous alternative embodiment, the emitting face 4 exhibits a focused geometry that is to say, that the ultrasonic waves generated are focused in a focal area either due to the control mode of the ultrasonic transmitters or due to the geometric form of the emitting face. Typically, the emitting face 4 has a concave form such as a hemispheric form and in the example illustrated in FIG. 2, a toric shape. Advantageously, the inner edge 4b delimits a housing 6 for an imaging probe 8 in particular. According to this embodiment example, the axis of acoustic propagation A corresponds to the axis of symmetry of the torus forming the emitting face 4 and is perpendicular to the plane passing by the peripheral edge 4a of the emitting face.

Figure 4:
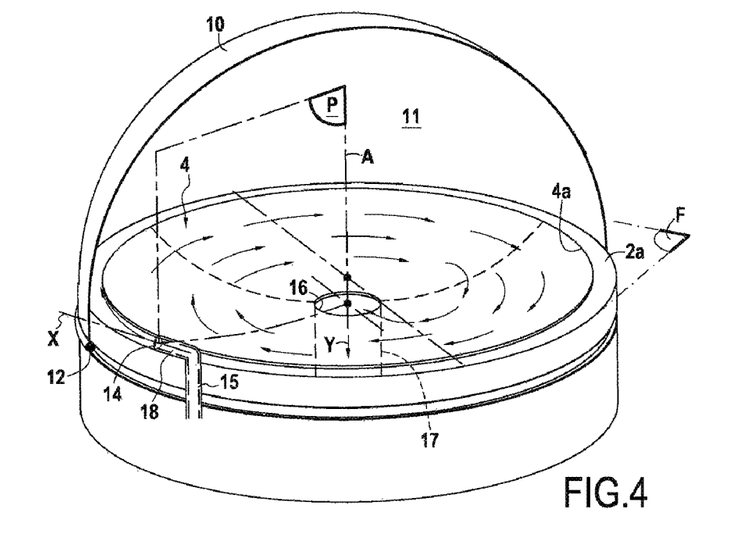
FIG. 4 is a block diagram of a probe in accordance with the invention showing the vortex cooling on a concave emitting face.

Obviously, the emitting face 4 can exhibit a form different from a concave form such as illustrated on FIGS. 2 and 4. In the examples illustrated on FIGS. 5A, 5B, 6, 7 and 9, the emitting face 4 exhibits a flat form. According to these embodiment examples, the axis of acoustic propagation A is perpendicular to the emitting face 4.

According to the embodiment examples illustrated by FIGS. 2, 4, 5A, 6, 7 and 9, the emitting face 4 exhibits a contour of circular form but it is clear that the emitting face can exhibit a contour of different form for example rectangular or oblong. In the example illustrated on FIG. 5B, the emitting face 4 is truncated in a symmetrical manner with respect to the axis of acoustic propagation A such that the emitting face 4 exhibits two rectilinear edges extending in parallel and facing each other and connected together by two circular edges having the same bend radius.

The probe 1 also includes a membrane 10 placed in front of the emitting face 4 and made from a transparent material with ultrasonic waves. This membrane 10 delimits with the emitting face 4, a cooling chamber 11, wherein a cooling fluid circulates. This membrane 10 is fastened on the body 2 by any appropriate means with an O-ring 12 to obtain a sealing cooling chamber. This cooling chamber 11 is also capable of taking an acoustic coupling function with the insonified medium. Typically, the cooling fluid is a water-based liquid that has been degassed to improve the propagation of the waves or oil selected from those having acoustic characteristics of low absorption of ultrasonic waves. The liquid described in patent EP 1038 551 can also be used.

The cooling chamber 11 includes at least one inlet 14 for the cooling fluid that is brought by at least one supply channel 15. Each inlet 14 is located at the periphery of the emitting face 4 outside the emitting face so as not to disrupt the propagation of ultrasonic waves. According to an advantageous characteristic of the embodiment, each inlet 14 is achieved in a crown 2a of the body 2 surrounding the transducer at the peripheral edge 4a of the emitting face 4. Each inlet 14 is hence located outside the emitting face 4, on the border of the peripheral edge 4a of the emitting face. In the embodiment examples illustrated on FIGS. 2, 4, 5A, 5B and 6, the cooling chamber 11 includes a unique inlet 14 whereas in the examples illustrated on FIGS. 7 and 9, the probe 1 includes several inlets 14.

The cooling chamber 11 also includes at least one outlet 16 located in the central part of said emitting face 4. Each outlet 16 includes an outlet duct 17 delimiting by its inlet orifice, a passage section for the cooling fluid exiting the cooling chamber. Each outlet 16 exhibits an outlet axis Y perpendicular to the straight passage section of the outlet duct 17 recovering the fluid exiting the cooling chamber 11. Thus, the outlet duct 17 exhibits by its orifice, a passage section which allows the discharge of the flow of cooling liquid according to the direction Y. The passage section of the outlet 16 can be of any possible form. The probe 1 includes a unique outlet 16 in the illustrated examples, except for the preferred example illustrated on FIG. 2 wherein the probe includes two outlets 16 located symmetrically on either side of the axis of acoustic propagation A of the emitting face.

In accordance with the invention, the probe 1 includes at the inlet 14, at least one guiding tubular duct 18 for the cooling fluid, communicating with the supply channel 15. This tubular duct 18 is adapted to create inside the cooling chamber 11, between the inlet 14 and the outlet 16, a swirling circulation or vortex of the cooling fluid around the axis of acoustic propagation A. This swirling circulation or vortex leads to a flow of cooling fluid which carries out at least a rotation turn around the axis of acoustic propagation A. Each fluid particle thus describes a rotational movement greater than 360° around the axis of acoustic propagation A. The terms swirling and vortex will be used interchangeably in the rest of the description to describe the phenomenon of circulation of the cooling fluid in relation to the emitting face of the transducer.

Advantageously, the swirling circulation of the cooling fluid is achieved around a rotation axis confounded with the axis of acoustic propagation A of the emitting face. Such is the case in particular when the outlet axis Y of the outlet 16 is confounded with the axis of acoustic propagation A of the emitting face.

Figure 3:
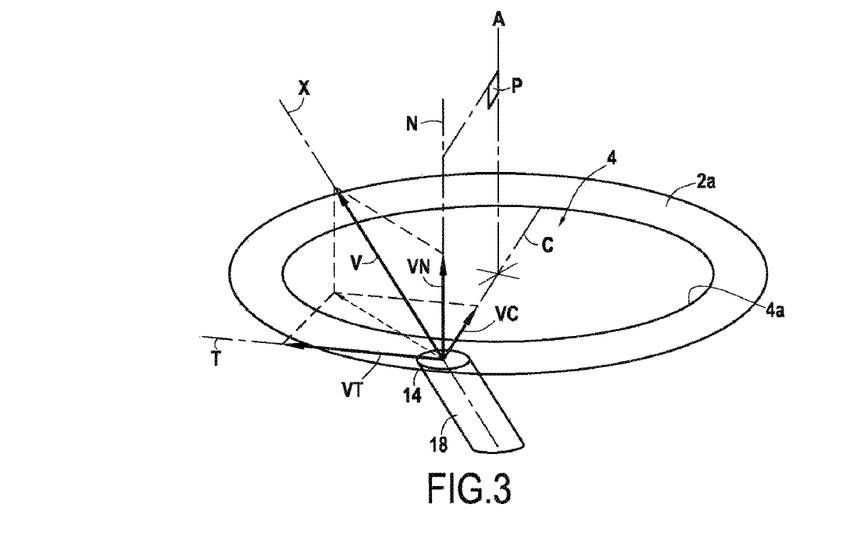
FIG. 3 is a diagram showing the vortex cooling principle of a probe in accordance with the invention.

It is worth noting that this tubular duct 18 for guiding the fluid, located at the inlet 14 allows to define by its end opening into the cooling chamber 11, a straight section of the inlet passage for the cooling fluid. This tubular duct 18 extends according to a longitudinal extension axis X by exhibiting a determined sufficient length suitable for channeling the flow of cooling fluid and giving it a velocity whereof the velocity vector V is collinear with the longitudinal extension axis X, that is to say perpendicular to the straight section of the inlet passage. Such as it appears more particularly from FIG. 3, this tubular duct 18 is oriented in a manner that its longitudinal extension axis X and thereby, the velocity vector that it bears, exhibits a non-null tangential component VT establishing itself according to a tangential direction T to create a swirling circulation of the cooling fluid inside the cooling chamber 11.

It is worth noting that the tangential direction T is considered with respect to the peripheral edge 4a of the emitting face 4, this tangential direction being one of the three orthogonal directions of a frame of reference including a normal orthogonal direction N to the plane containing the peripheral edge 4a of the emitting face 4, and a centripetal direction C orthogonal to the tangential direction T and directed towards the centre of the emitting face. This tangential direction T is substantially orthogonal to a plane P containing the axis of acoustic propagation A and at least a point of the inlet 14 that is to say, for example the intersection point of the longitudinal extension axis X with the straight section of the inlet passage defined by the tubular duct 18.

As stated above, the tubular duct 18 is oriented in such a manner that its longitudinal extension axis X and thereby the velocity vector that it bears exhibits a non-null tangential component VT, being established according to a tangential direction T. Generally, this velocity vector V is decomposed as illustrated on FIG. 3, according to the three directions of the frame of reference, namely, a tangential direction T, a centripetal direction C and a normal direction N, into three components, respectively, a tangential component VT, a centripetal component VC and a normal component VN.

This tubular duct 18 has, starting from its end, a length determined according to the longitudinal extension axis X for channeling the cooling fluid and giving it a suitable orientation and velocity for obtaining the swirling circulation of the cooling fluid. Thus, the cooling fluid exhibits at the straight section of the inlet passage, a velocity vector V with an orientation according to the longitudinal extension axis X and whereof the tangential component VT is non null.

It emerges from the previous description that the tubular duct 18 is arranged to optimise the tangential component VT with respect to the other components. Ideally, the tubular duct 18 is arranged so that the centripetal VC and normal VN components are null or tend towards null values.

Thus, this tubular duct 18 is oriented in such a manner that its longitudinal extension axis X and the velocity vector that it bears exhibits a tangential component such that the ratio of the tangential component of the velocity vector on the centripetal component of the velocity vector is greater than 1.

Ideally, the length of the tubular duct 18 should be greater or equal to its diameter for a tubular duct of circular section. By way of example, the tubular duct 18 of FIG. 2 is circular and exhibits a length of 20 mm and a mean diameter of 2 mm whereas that of FIG. 4 exhibits a length of 3 mm and a diameter of 1 mm. If the tubular duct exhibits a non circular section but oblong or rectangular such as that represented on FIGS. 8A and 8B, the length of the tubular duct should be greater than or equal to the smallest diameter of the oblong section or greater than or equal to the smallest width of the rectangular section. Preferably, the length of the tubular duct 18 is greater by 1.5 times its diameter for a duct of circular section. Likewise, the length of the tubular duct 18 is greater than by 1.5 times the smallest diameter of an oblong section or the smallest width of the rectangular section.

Thus, it is created a vortex circulation of the cooling fluid around an axis of acoustic propagation A, between the inlet 14 located at the periphery of the emitting face 4 and the outlet 16 located in the central part of the emitting face 4. The velocity vector V of the cooling fluid exhibits at the inlet passage section 14, a direction whereof a component VT is non null and substantially perpendicular to the plane P. Thus, the cooling fluid takes a tangential direction with respect to the edge 4a of the emitting face 4 to create a swirling circulation of the cooling fluid inside the cooling chamber 11.

The implementation at the inlet 14, of at least one tubular duct 18 allows creating, in combination with the outlet 16, this vortex circulation of the cooling fluid in the cooling chamber 11. It is worth noting that the channel 15 for supplying cooling fluid includes a device for controlling the velocity of the fluid allowing to impart the cooling fluid at the inlet in the cooling chamber, a sufficient adapted velocity for obtaining a swirling circulation. Typically, a fluid velocity at the inlet 14 ranges between $10^{-3}$ m/s and 1 m/s.

According to an advantageous alternative embodiment wherein the probe includes a temperature sensor adapted for measuring the temperature of the rear face of the transducer, the temperature sensor is connected to the device for controlling the fluid velocity allowing to control the inlet velocity of the fluid in the cooling chamber according to the measurement performed by the temperature sensor.

This swirling circulation is carried out whatever the form of the emitting face 4. By way of example, the FIG. 4 illustrates the swirling circulation of the cooling fluid for a concave emitting face 4 whereas FIGS. 5A, 5B, 6, 7 and 9 show the swirling circulation for a planar emitting face 4.

It should be understood that the object of the invention allows obtaining an optimised and homogenous cooling over the entire surface of the emitting face 4. As explained previously, the swirling circulation or vortex of the cooling fluid around the axis of acoustic propagation A implements a unique swirl.

The circulation of cooling fluid according to a unique swirl allows, from a macroscopic point of view, to maintain a laminar displacement of the cooling fluid, ensuring a homogenous cooling over the entire surface of the emitting face 4. Furthermore, from a microscopic point of view, the circulation in the form of a swirl increases the cooling efficiency that would be obtained by direct, non swirling circulation of the cooling fluid between an inlet point 14 and an outlet point 16. The obtained swirl allows each particle of cooling fluid to perform at least one rotation turn around the axis of acoustic propagation A. Generally, each particle of cooling fluid turns between the inlet 14 and the outlet 16, according to several turns around the axis of acoustic propagation A. The number of turns of the fluid particle and hence, its displacement velocity will be all the more important when the ratio of the tangential velocity component on the centripetal velocity component is much greater than 1. This ratio tends to infinity when the centripetal velocity component is null as illustrated on FIG. 4.

According to a first embodiment, the guiding duct 18 of the fluid is achieved by a part of the supply channel 15 of the cooling fluid opening by the inlet 14 in the cooling chamber 11. As it appears more precisely on FIG. 4, the supply channel 15 includes upstream of the inlet 14, the tubular duct 18 oriented tangentially with respect to the edge 4a of the emitting face 4. According to this example, the supply channel 15 includes a part that extends substantially parallel to the axis of acoustic propagation A ending by a bent part at 90° forming the tubular duct 18 for guiding the cooling fluid. This bent part at 90° forming the tubular duct 18 allows to delimit at its end, the straight section of the inlet passage for the cooling fluid. The normal of this straight section of the inlet passage corresponds to the longitudinal extension axis X which is oriented according to the tangential direction T substantially orthogonal to the plane P containing the axis of acoustic propagation A. With this arrangement taken into account, the velocity vector V of the cooling fluid is substantially decomposed into a tangential component VT, according to the tangential direction T with respect to the edge 4a of the emitting face 4.

Obviously, the supply channel 15 can be completely oriented tangentially with respect to the edge 4a of the emitting face 4, even is this solution is more cumbersome as the supply channel 15 and the outlet duct 17 are, in this case, orthogonal.

Figure 5A:
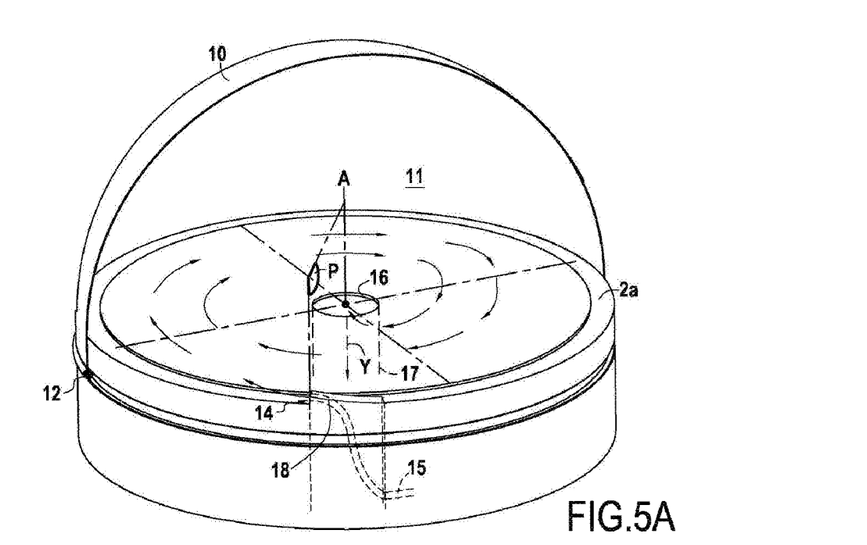
FIG. 5A is a block diagram of a probe in accordance with the invention showing the vortex cooling on a circular flat emitting face.
Figure 5B:
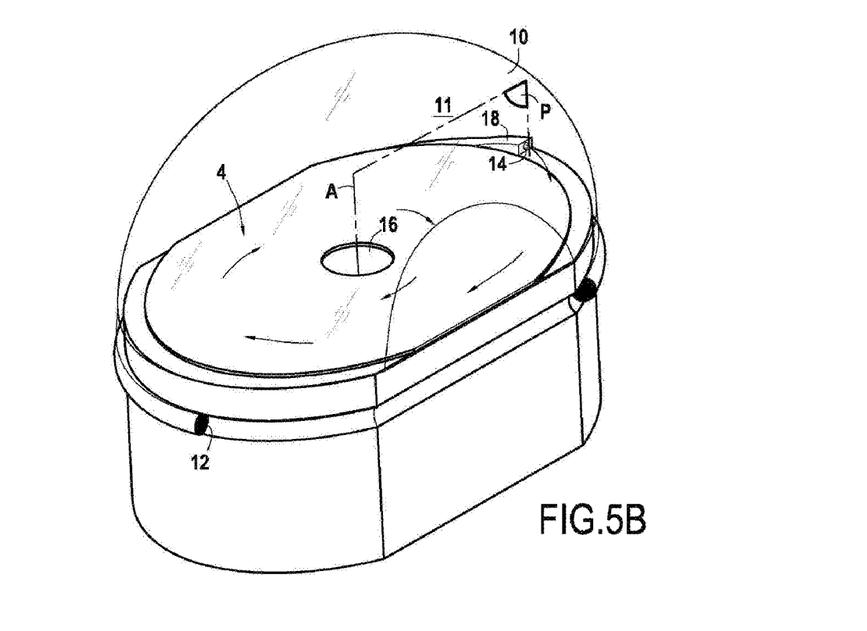
FIG. 5B is a block diagram of a probe in accordance with the invention showing the vortex cooling on a non circular flat emitting face.

According to another embodiment example illustrated on FIG. 5A, the supply channel 15 includes upstream of the inlet 14, a part 18 forming the tubular duct and oriented at the outlet, tangentially with respect to the edge 4a of the emitting face 4. According to this example, the supply channel 15 includes a part that extends substantially perpendicularly to the outlet axis by extending by a bent part 18 forming the tubular duct and defining at its end, the inlet passage section whereof the normal is orthogonal to the plane P. Even there, the velocity vector V of the cooling fluid is decomposed substantially into a tangential component VT, according to the tangential direction T with respect to the emitting face 4.

In the embodiment examples illustrated on FIGS. 4, 5A, 5B and 7, the tubular duct 18 is located beyond the frontal plane F of the emitting face 4, this frontal plane F passing by the peripheral edge 4a of this emitting face. According to these examples, the supply channel 15 includes in is terminal part, the tubular duct 18 which is oriented to exhibit a straight passage section perpendicular to the frontal plane and located in front of this frontal plane such as to obtain a flow of cooling fluid with a velocity that is collinear with the tangential direction T.

Figure 6:
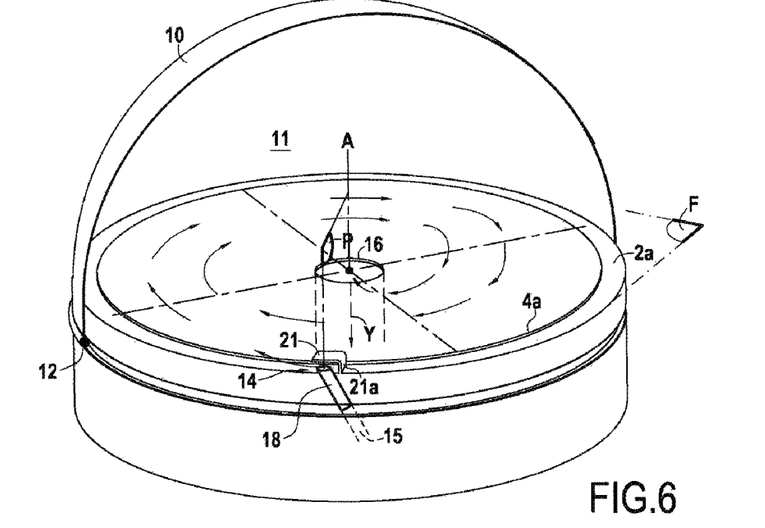
FIG. 6 illustrates another embodiment of a probe in accordance with the invention showing the vortex cooling using a deflector.

According to a second embodiment whereof the principle is illustrated on FIG. 6, the tubular duct 18 is set back or at the frontal plane F of the emitting face 4, passing by the peripheral edge 4a of this emitting face. In other words, the tubular duct 18 of the cooling fluid opens into the crown 2a of the support located in the frontal plane of the emitting face in such a manner that the end of the tubular duct 18 and the peripheral edge 4a of the emitting face are located at the same level.

According to this second embodiment, the tubular duct 18 is oriented in such a manner that its longitudinal extension axis X and after, the velocity vector V exhibits a non null tangential component establishing itself according to a tangential direction T for creating a swirling circulation of the cooling fluid inside the cooling chamber 11. According to this configuration, the longitudinal extension axis X and after the velocity vector of the fluid also exhibits a normal component establishing itself according to the normal direction N. According to this example, the probe includes at the inlet, at least one wall 21 for deflecting the fluid arranged facing the outlet of the tubular duct to orient the fluid according to the tangential direction T. The amplitude of the normal component of the velocity vector is thereby, limited.

This defecting wall or deflector 21 is arranged in the cooling chamber 11 facing the tubular duct 18 and the support crown 2a. As it appears more precisely on FIG. 6, this deflector 21 constitutes an obstacle when the cooling fluid arrives inside the chamber, brought by the tubular duct 18. In combination with the support crown 2a, this deflector 21 thus forces the cooling fluid to take a tangential direction with respect to the emitting face. This deflector 21 thus includes a frontal part oriented according to the tangential direction T located facing the outlet of the tubular duct 18.

According to an advantageous alternative embodiment, the deflector 21 is extended at a right angle by a stop part 21a allowing to orient the cooling fluid in a unique tangential sense.

FIG. 2 illustrates an alternative embodiment of this principle wherein the emitting face 4 includes a circular peripheral edge 4a which is bordered at its periphery by a peripheral channel 28 communicating with one or several tubular ducts 18 for supplying cooling fluid opening into the crown 2a. The tubular ducts 18 of the cooling fluid open into the peripheral edge 2a of the support located in the frontal plane of the emitting face such that the end of the tubular ducts 18 and the peripheral edge 4a of the emitting face are located at the same level.

Figure 8A:
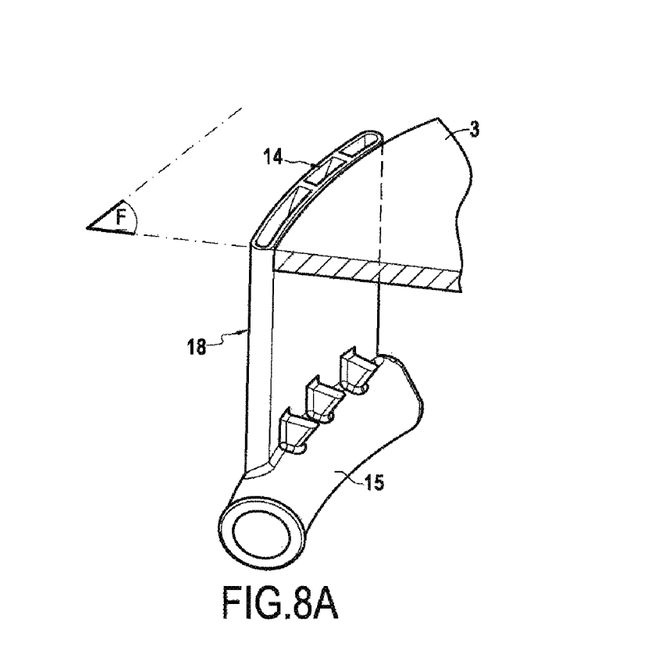
FIG. 8A illustrates a detailed view of an embodiment example of an inlet of cooling fluid of a probe according to the invention.
Figure 8B:
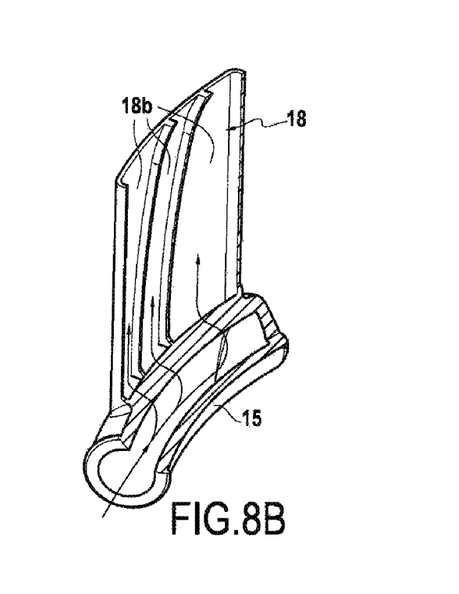
FIG. 8B illustrates a detail of the cooling fluid supply duct for the inlet illustrated on FIG. 8A.

As it emerges more particularly from FIGS. 8a to 8B, the channel 15 for supplying cooling fluid communicates with a tubular duct 18 opening into the crown 2a. To reduce head loss linked to the tubular duct 18 without however having to increase its section, the tubular duct 18 advantageously includes several parallel channeling routes 18b, in the illustrated example, 3 routes, provided to espouse the circular form of the crown 2a. This tubular duct 18 thus opens according to a limited sector of the circumference of the peripheral edge 4a of the emitting face.

For each inlet, the cooling fluid is guided according to the tangential direction, by the tubular duct 18 but also by a deflecting wall 2b located facing and at a distance from the outlet section of the tubular duct 18. This deflecting wall 2b acts as a deflector for the cooling fluid to orient the fluid according to the tangential direction such that the amplitude of the normal component of the velocity vector is thus limited.

In the illustrated example, the deflecting wall 2b is achieved in the form of an annular border extending facing the crown 2a of the support. The crown 2a of the support is connected to the annular border 2b by means of a connecting wall 2c. The annular border 2b that extends facing and at a distance from the crown 2a delimits a peripheral channel 28 achieved, as explained above, by a groove provided in the body 2 so as to close outside the chamber and communicate internally with the central part of the cooling chamber.

The peripheral channel 28 includes punctual studs 29 for mechanically linking the crown 2a of the support and the annular border 2b. In the embodiment example illustrated on FIGS. 9 and 10, the studs 29 are each achieved in the form of a wing for diverting the cooling fluid. The space between each stud thus forms a centripetal opening providing access to the cooling chamber 11.

Figure 9:
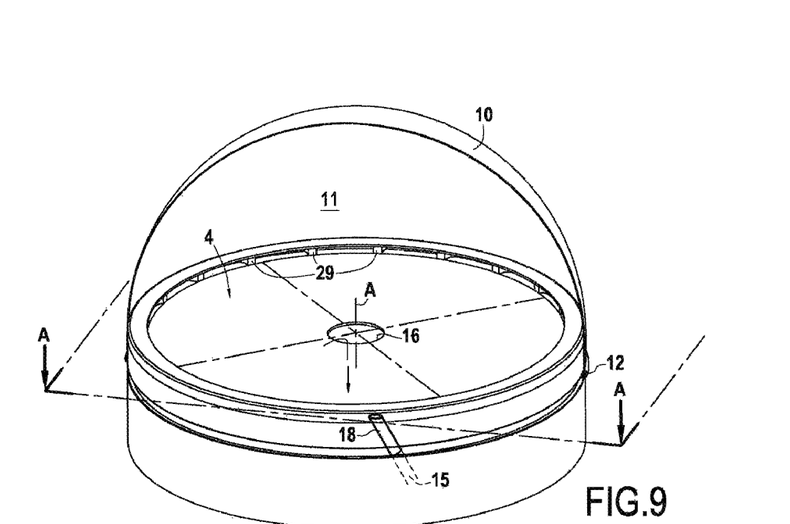
FIG. 9 illustrates another embodiment example of a cooling chamber including several inlets.
Figure 10:
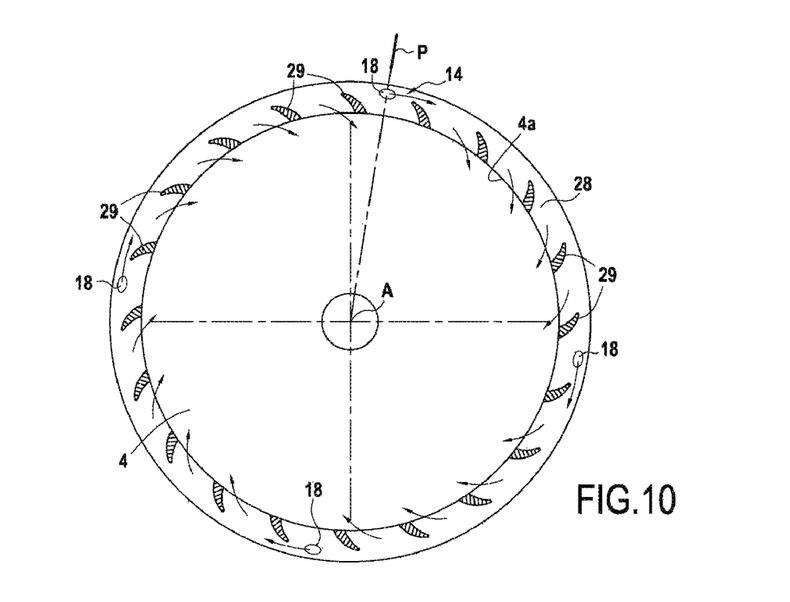
FIG. 10 is a sectional view taken substantially according to lines A-A of FIG. 9.

Each stud 29 has a curved profile varying from a tangent direction to a quasi-radial direction in order to limit head losses.

Figure 7:
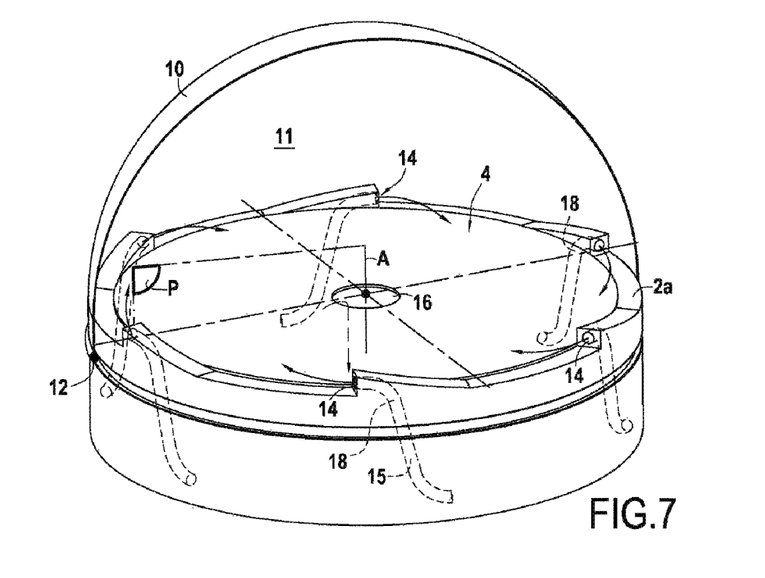
FIG. 7 illustrates another embodiment example of a cooling chamber including several inlets.

According to an alternative embodiment illustrated on FIG. 7, the cooling chamber 11 includes a series of inlets 14 distributed at the periphery of the emitting face 4, each one exhibiting at least a tubular duct 18 for guiding the fluid, oriented according to a direction orthogonal to the plane P containing the axis of acoustic propagation A, to create together a swirling circulation of the cooling fluid inside the cooling chamber. Obviously, all alternatives of the probe according to the invention can be equipped with several inlets.

In the examples illustrated on FIGS. 4, 5A, 5B, 6, 7 and 9, the cooling chamber 11 includes a unique outlet 16 whereof the outlet axis Y is confounded with the axis of acoustic propagation A of the emitting face 4.

According to the alternative embodiment illustrated on FIG. 2, the transducer 3 includes in its central part, a second outlet 16 for the cooling fluid. The two outlets 16 are arranged symmetrically on either side of the axis of acoustic propagation A of the emitting face 4 with an outlet axis Y collinear with the axis of acoustic propagation A of the emitting face 4. Obviously, all alternatives of the probe according to the invention can be equipped with several outlets. According to this alternative, the cooling fluid also circulates according to a unique swirling turning around the axis of acoustic propagation A.

It emerges from the preceding description that the object of the invention proposes a new method for cooling a transducer of a probe that generates ultrasonic waves, consisting in creating between the inlet and the outlet of the cooling chamber of the emitting face, a swirling circulation of the cooling fluid inside the cooling chamber around an axis perpendicular to the central part of the transducer. This vortex circulation namely a circulation according to a unique swirling improves at the same time the performance and homogeneity of the cooling by conduction of the therapeutic ultrasonic probe or even an imaging probe placed in its centre.

Obviously, the object of the invention can also be implemented to cool the rear face of the transducer.

The invention is not limited to the examples described and represented as diverse modifications can be brought thereto without departing from the scope of the invention.

The invention claimed is:

1. A method for cooling a transducer of a probe for generating ultrasonic waves, the transducer exhibiting, at the front, a face for emitting ultrasonic waves with an axis of acoustic propagation, and, at the rear, a rear face, at least the emitting face partially delimiting a cooling chamber wherein a cooling liquid is brought, through the tubular duct extending upstream of an inlet, with a length determined according to a longitudinal extension axis to channel the cooling fluid with a velocity vector decomposed into three components, respectively, a tangential component, a centripetal component, and a normal component, the cooling liquid circulating between at least the inlet and at least an outlet located in the central part of said emitting face, and orienting the tubular duct so that the longitudinal extension axis of the tubular duct and the velocity vector exhibit a tangential component, such that the ratio of the tangential component of the velocity vector on the centripetal component of the velocity vector is greater than 1, for creating, between the inlet located at the periphery of the emitting face and the outlet, a circulation of the cooling fluid according to a swirling inside the cooling chamber around the axis of acoustic propagation of the emitting face of the transducer.

2. An ultrasonic wave generating probe, including a transducer exhibiting, at the front, a face for emitting ultrasonic waves with an axis of acoustic propagation for propagating ultrasonic waves, and, at the rear, a rear face, at least the emitting face partially delimiting a cooling chamber wherein a cooling liquid is brought, through a tubular duct, to circulate between at least an inlet and at least an outlet located in the central part of said emitting face, the tubular duct extending upstream of the inlet, with a length determined according to a longitudinal extension axis to channel the cooling fluid with a velocity vector, decomposed into three components, respectively, a tangential component, a centripetal component, and a normal component, wherein the tubular duct is oriented such that the longitudinal extension axis exhibits a tangential component establishing itself according to a tangential direction substantially orthogonal to a plane containing the axis of acoustic propagation and the inlet, and such that the ratio of the tangential component of the velocity vector on the centripetal component of the velocity vector is greater than 1, for guiding the fluid with a view to creating a circulation of cooling fluid according to a swirling inside the cooling chamber.

3. The ultrasonic probe according to claim 2, comprising, at the inlet, at least one wall for deflecting the fluid arranged facing the outlet of the tubular duct to orient the fluid according to the tangential direction.

4. The ultrasonic probe according to claim 3, wherein the emitting face includes a peripheral edge located in a plane opening into an outlet, the tubular duct for guiding the cooling fluid, a fluid deflecting wall being arranged facing the outlet of the tubular duct.

5. The ultrasonic probe according to claim 4, wherein the peripheral edge of the emitting face is bordered at its periphery by a peripheral channel communicating with at least a tubular duct for supplying cooling fluid, this channel being provided with at least one centripetal opening for communicating with the cooling chamber.

6. The ultrasonic probe according to claim 5, comprising a plurality of centripetal communication openings each delimited between two neighbouring wings for diverting the cooling fluid, with a curving profile varying from one tangent direction to a quasi-radial direction.

7. The ultrasonic probe according to claim 2, wherein the probe includes a tubular duct for supplying cooling fluid and opening into the cooling chamber, and exhibiting a straight passage section whereof the normal is confounded with the tangential direction.

8. The ultrasonic probe according to claim 2, wherein the cooling chamber includes a series of inlets distributed at the periphery of the emitting face, each one exhibiting at least a tubular duct for the fluid, oriented according to a direction for creating together a swirling circulation of the cooling fluid inside the cooling chamber.

9. The ultrasonic probe according to claim 2, wherein the emitting face exhibits a focusing geometry.

10. The ultrasonic probe according to claim 9, wherein the emitting face is truncated symmetrically with respect to an axis of acoustic propagation.

11. The ultrasonic probe according to claim 2, wherein the transducer includes, in its central part, a second outlet for the cooling fluid, the two outlets being arranged symmetrically on either side of the axis of acoustic propagation of the emitting face.

12. The ultrasonic probe according to claim 11, wherein the transducer includes, in its central part, a cutout delimiting a housing for an imaging probe, on either side of which are located the outlets for the cooling fluid.

13. The ultrasonic probe according to claim 2, wherein the probe includes a fluid supply duct opening by the inlet in the cooling chamber, this duct including a device for controlling fluid velocity.

14. The ultrasonic probe according to claim 13, comprising a temperature sensor adapted for measuring the temperature of the rear face of the transducer, this temperature sensor being connected to the device for controlling the fluid velocity allowing to control the inlet velocity of the fluid in the cooling chamber according to the temperature measurement.

15. The ultrasonic probe according to claim 2, wherein the tubular duct exhibits a length greater than, or equal to, either its diameter for a duct of circular section, or the smallest diameter for a duct of oblong section, or the smallest width for a duct of rectangular section.

* * * * *